(12) United States Patent
Wall, III et al.

(10) Patent No.: US 8,529,477 B2
(45) Date of Patent: *Sep. 10, 2013

(54) CONTROL AND INTEGRATION OF SENSORY DATA

(75) Inventors: Conrad Wall, III, Boston, MA (US); Lars I. E. Oddsson, Boston, MA (US); Peter Francis Meyer, Shrewsbury, MA (US)

(73) Assignees: Massachusetts Eye & Ear Infirmary, Boston, MA (US); The Trustees of Boston University, Boston, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/567,975

(22) Filed: Aug. 6, 2012

(65) Prior Publication Data

US 2013/0030330 A1  Jan. 31, 2013

Related U.S. Application Data

(63) Continuation of application No. 11/609,007, filed on Dec. 11, 2006, now Pat. No. 8,235,918.

(51) Int. Cl.
- *A61B 5/103* (2006.01)
- *A61B 5/117* (2006.01)
- *A61B 5/00* (2006.01)
- *A61N 1/00* (2006.01)
- *G01C 9/00* (2006.01)

(52) U.S. Cl.
USPC ............ 600/595; 600/301; 607/62; 73/865.4; 702/151

(58) Field of Classification Search
USPC ................ 600/300, 587, 595; 607/48, 49, 607/62; 623/24, 25; 702/19, 151–154; 73/865.4

See application file for complete search history.

(56) References Cited

U.S. PATENT DOCUMENTS

| | | | | |
|---|---|---|---|---|
| 5,919,149 | A * | 7/1999 | Allum | 600/595 |
| 6,063,046 | A * | 5/2000 | Allum | 600/595 |
| 6,307,481 | B1* | 10/2001 | Lehrman et al. | 340/669 |
| 6,546,291 | B2* | 4/2003 | Merfeld et al. | 607/62 |
| 7,313,440 | B2* | 12/2007 | Miesel | 607/19 |
| 8,235,918 | B2* | 8/2012 | Wall et al. | 600/595 |
| 2003/0171791 | A1* | 9/2003 | KenKnight et al. | 607/60 |
| 2006/0167647 | A1* | 7/2006 | Krumm et al. | 702/130 |
| 2008/0039756 | A1* | 2/2008 | Thorsteinsson et al. | 602/23 |

* cited by examiner

*Primary Examiner* — Max Hindenburg
*Assistant Examiner* — John Pani
(74) *Attorney, Agent, or Firm* — Fish & Richardson P.C.

(57) ABSTRACT

A sensory data integration system for integrating sensory data generated by a first sensory substitution device and sensory data generated by a second sensory substitution device. The system includes a processor configured to generate an orientation signal indicative of a difference between a subject's orientation and an acceptable orientation. The orientation signal is based on the sensory data generated by the first sensory substitution device and the sensory data generated by the second sensory substitution device.

15 Claims, 9 Drawing Sheets

CONTROL AND INTEGRATION OF SENSORY DATA

CROSS-REFERENCE TO RELATED APPLICATION

This application is a continuation application of U.S. patent application Ser. No. 11/609,007, filed on Dec. 11, 2006, issuing as U.S. Pat. No. 8,235,918, on Aug. 7, 2012, the entire contents of each of which are incorporated by reference.

TECHNICAL FIELD

This disclosure relates to sensory prostheses, and in particular, to balance prostheses.

BACKGROUND

The soles of one's feet, together with the vestibular system of one's inner ear, provide cues about self-motion. The central nervous system processes these motion cues, together with those provided by the feet, vestibular system, and other body parts to estimate self-motion in 6 degrees of freedom: three of which are angular and three of which are linear.

In some cases, injury, disease, or prolonged exposure to altered gravity disrupts the flow of sensory information, resulting in dizziness, blurred vision, inability to orient correctly (including the ability to align with the vertical), and reduced ability to stand or walk.

Balance prostheses have been developed in an effort to improve postural stability in the balance impaired. Uses for balance prostheses include: (1) a balance "pacemaker" to reduce dizziness and imbalance due to abnormal fluctuations in the peripheral vestibular system, (2) permanent replacement of vestibular or balance function, (3) temporary replacement of motion cues that commonly occur following ablative surgery of the inner ear, and (4) vestibular/balance rehabilitation.

Balance prostheses may be implantable or non-implantable. An implantable prosthesis delivers self-motion cues to the central nervous system via implanted stimulators. Non-implantable prostheses are a less invasive means of providing some self-motion cues. Such prostheses operate by, for example, stimulating the vestibular nerve via surface electrodes or by displaying self-motion cues using "sensory substitution" (e.g., acoustic inputs or electric currents applied to the tongue). (See P. Bach-y-Rita, "*Late post-acute neurologic rehabilitation: neuroscience, engineering and clinical programs,*" Arch Phys. Med. Rehab, Vol. in press, 2002, and P. Bach-y-Rita, K. A. Kaczmarek, et al., "*Form perception with a 49-point electrotactile stimulus array on the tongue: a technical note,*" J Rehabil Res Dev, Vol. 35, No. 4, 1998, p. 427-30.) Stimulation using auditory cues is described in U.S. Pat. No. 5,919,149 ("the '149 patent"), the full disclosure of which is incorporated by reference herein.

U.S. Pat. No. 6,546,291, the full disclosure of which is incorporated herein by reference, describes vestibular prostheses that include tactile vibrators (tactors) mounted on the subject's torso.

SUMMARY

In general, in one aspect, a sensory data integration system for integrating sensory data generated by a first sensory substitution device and sensory data generated by a second sensory substitution device, the system includes: a processor configured to generate an orientation signal indicative of a difference between a subject's orientation and an acceptable orientation, the orientation signal being based on the sensory data generated by the first sensory substitution device and the sensory data generated by the second sensory substitution device.

Implementations may include one or more of the following features. The sensory data integration system also includes a stimulator configured to present a stimulus to a subject based on the orientation signal. The stimulus includes a visual stimulus. The stimulus includes a tactile stimulus. The stimulus includes an audio stimulus. The stimulus includes electrical stimulus. The processor is configured to determine a context of a subject using the sensory data integration system. The first device has a set-point, and the processor is configured to update the set-point based on the sensory data generated by the first or second sensory substitution device. The first device has a set-point, and the processor is configured to update the set-point based on the context. The sensory data integration system also includes a stimulator configured to present a stimulus to a subject based on the context. The processor is configured to deactivate the first sensory substitution device based on the context.

In general, in another aspect, providing cues to a balance-impaired subject includes: obtaining first data from a first sensory substitution device; obtaining second data from a second sensory substitution device; determining an acceptable state of the subject based on the first set and the second set of data; providing an orientation cue to the subject based on the acceptable state, the first data, and the second data, with the cue being indicative of the acceptable state.

Implementations include one or more of the following features. Providing the orientation cue includes providing a tactile cue. Providing the orientation cue includes providing an audio cue. Providing the orientation cue includes providing a visual cue. Providing the orientation cue includes providing an electrical cue. Providing cues to a balance-impaired subject also includes determining a context of the subject based on the first data and the second data. The acceptable state is determined based on the context. The orientation cue is provided based further on the context. Providing cues to a balance-impaired subject also includes deactivating the first sensory substitution device based on the context.

In general, in another aspect, a balance prosthesis includes: a first sensory substitution device that generates a first set of sensory data and has a first set-point; a second sensory substitution device that generates a second set of sensory data and has a second set-point; an integration system in communication with the first sensory substitution device and the second sensory substitution device, the integration system including: a processor configured to generate an orientation signal based on the first and second sets of sensory data, and to update the first set-point based on the first and second sets of sensory data.

Other aspects include other combinations of the features recited above and other features, expressed as methods, apparatus, systems, program products, and in other ways. Other features and advantages will be apparent from the description and from the claims.

DETAILED DESCRIPTION

Figure 1:
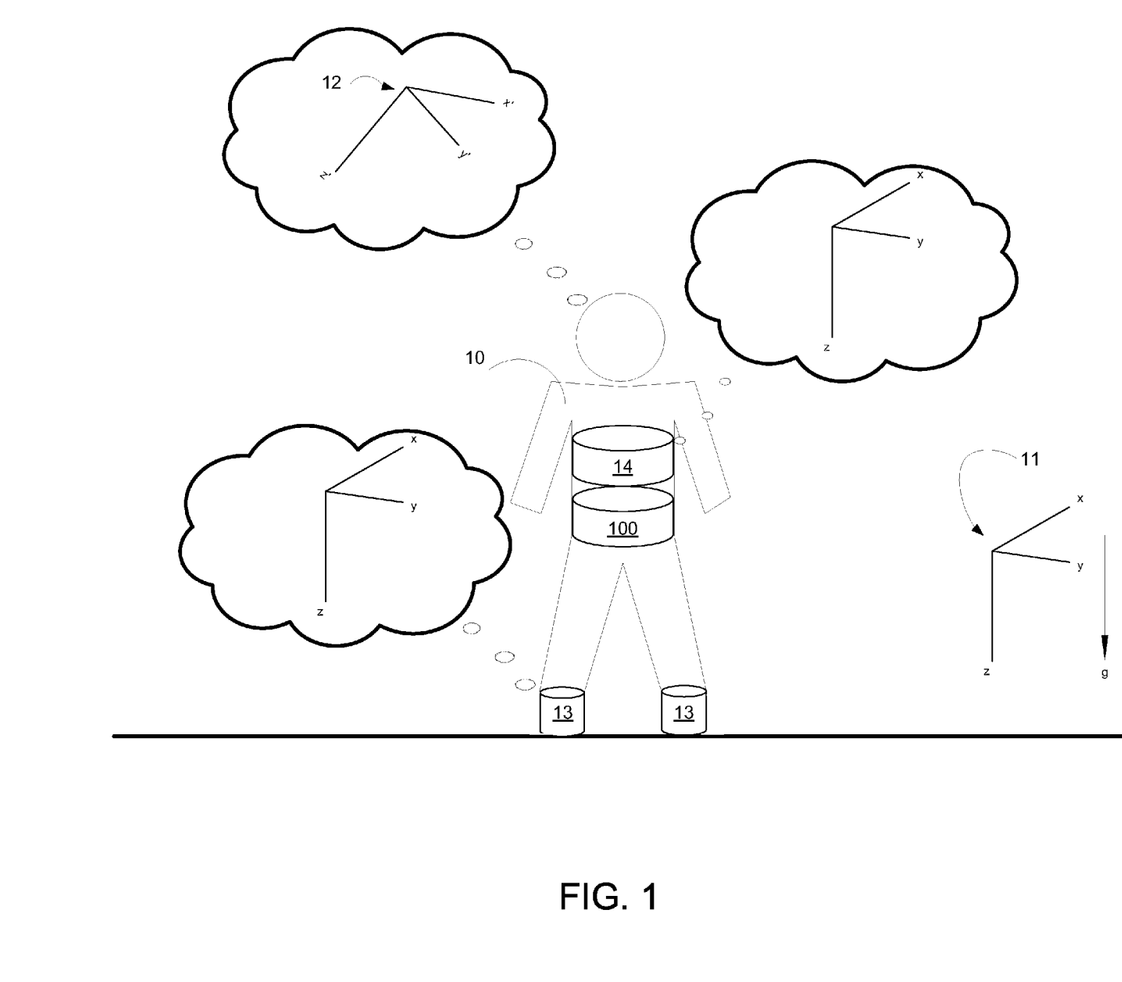
FIG. 1 shows a balance-impaired subject wearing a sensory substitution integration system and sensory substitution devices.

FIG. 1 shows a balance impaired subject 10 standing upright on flat ground, generally parallel to the direction of the force of gravity g. A reference Cartesian coordinate system 11 (x, y, z) is shown, with z parallel to the direction of gravity, and the x-y plane parallel to the ground. Although the subject may actually be standing generally parallel to the z-axis, due to his balance impairment, he may "feel" as if he is standing generally parallel to another axis, z', in a sensed coordinate system 12.

To assist him in coping with or overcoming his balance impairment, the subject wears sensory substitution devices, 13, 14. In the absence of an integration system 100, a sensory substitution device measures physical characteristics of the subject or his environment that are indicative of the subject's or environment's physical properties, for example the subject's orientation. Each sensory substitution device 13, 14 measures physical characteristics of the subject and the environment that are compared with pre-determined values or ranges of values. Despite the use of the term "substitution," the sensory substitution devices 13, 14 can do more than merely replace sensory data that would otherwise be available to the subject but for an impairment. Instead, sensory substitution devices 13, 14 can enhance a subject's sensory range or accuracy beyond normal human levels. For example, the sensory substitution device 13 may include a microphone that is more sensitive than a typical person's normally-functioning ear.

Each sensory substitution device 13, 14 measures physical characteristics of the subject and the environment are compares these measurements with pre-determined values or ranges of values. The pre-determined values or ranges of values are indicative of an acceptable state of the subject in the environment; e.g., the subject having an axis aligned with the vertical. If there is a deviation from the pre-determined value or range of values, the sensory substitution device provides motion cues to the subject. These motion cues tell the subject how to achieve the acceptable state. To integrate sensory substitution devices, a sensory-data integration system 100 is connected to the sensory substitution devices 13, 14. As will be described more fully below, the integration system 100 infers the subject's state and his activities based on the outputs of the individual sensory substitution devices 13, 14.

Although the subject is shown using only two sensory substitution devices 13, 14, any number of sensory substitution devices may be used. Additionally, each sensory substitution device may provide data limited to only a portion of the subject's body, e.g. his torso. Sensory substitution devices 13, 14 may include any sensing equipment capable of sensing the subject or the subject's environment. Examples include: a photocell configured to detect levels of brightness in the environment; an accelerometer or gyroscope configured to detect acceleration in the subject or a portion of the subject; a vibratometer configured to detect vibration in the subject or a portion of the subject; a thermometer configured to detect the temperature of the subject, a portion of the subject, or the ambient temperature of the subject's environment; an altimeter configured to detect the altitude of the subject; a magnetometer configured to measure an ambient magnetic field (e.g., in a magnetic compass); a level or a float switch configured to detect a subject's spatial orientation; a positioning receiver or transmitter, such as those used with global positioning satellites (GPS), configured to detect the subject's location on Earth, or the subject's proximity to a positioning beacon; a moisture sensor configured to detect humidity or moisture in the subject's environment, or electromyography equipment configured to detect activity in any of the subject's muscles.

In an exemplary embodiment, the first sensory substitution device 13 generally resembles a sock that determines the subject's orientation by detecting the distribution of pressure on the subject's foot. In this document, such a device will be called a "sock." The second sensory substitution device 14 generally resembles a vest that uses accelerometers and gyroscopes to determine the subject's orientation. In this document, such a device will be called a "vest."

Figure 2A:
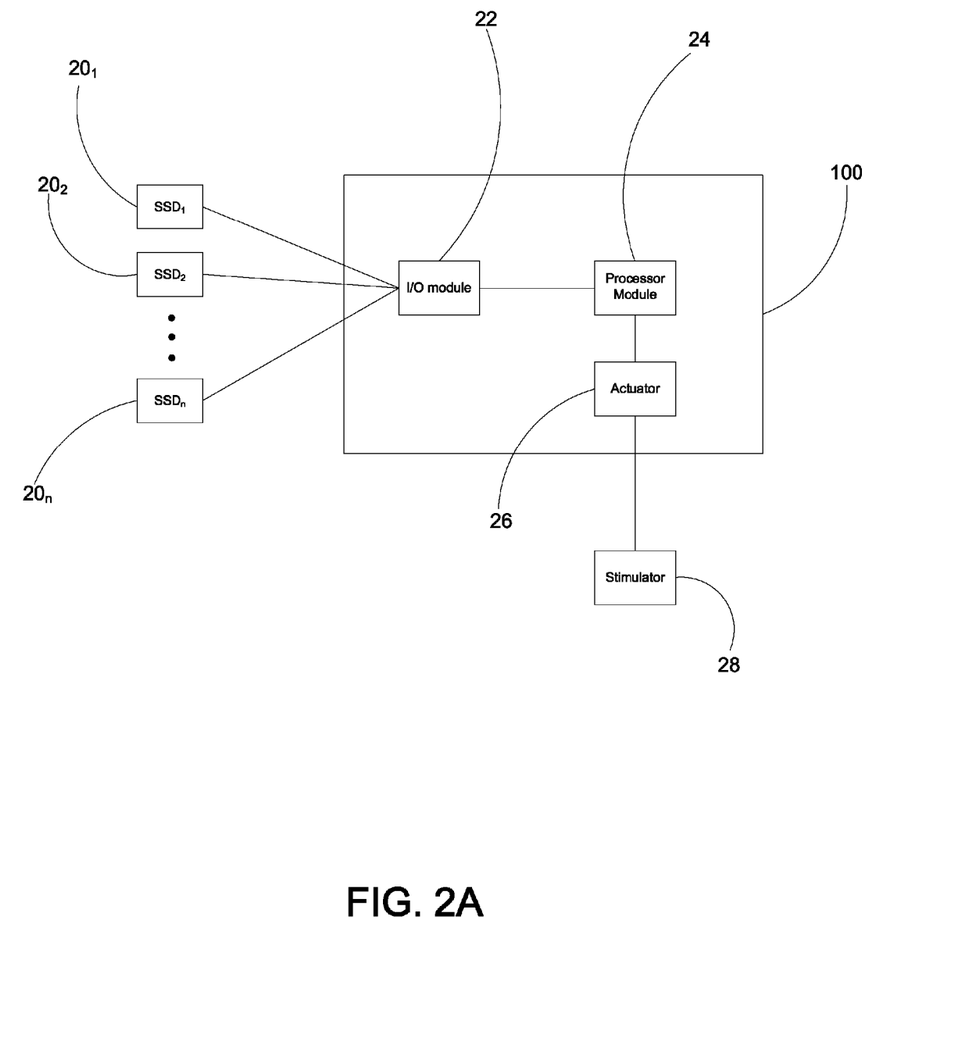
FIG. 2A-C are block diagrams of sensory data integration systems.

Referring to FIG. 2A, the integration system 100 has an input/output module 22, that receives orientation data provided by individual sensory substitution devices $20_1, 20_2, \ldots, 20_n$. The input/output module 22 organizes the orientation data received by the devices $20_1, 20_2, \ldots, 20_n$ and sends the organized orientation data to a processor module 24.

As will be described below, the processor module 24 uses the orientation data determined by the devices $20_1, 20_2, \ldots, 20_n$ to determine the subject's current state, the acceptable range of states for the subject, whether the subject's current state is acceptable, and how the subject should move to correct his state if necessary. As used herein, "state" refers to the ensemble of physical characteristics detectable by any of the various sensory substitution devices, $20_1, 20_2, \ldots, 20_n$. In the exemplary embodiment in which the sensory substitution devices $20_1, 20_2, \ldots, 20_n$ include a vest and a sock, the subject's state can include (but is not limited to) the subject's orientation, the orientation of parts of the subject (e.g., angle of torso relative to the ground), the subject's total weight (e.g., the weight of the subject plus the weight of a carried load), or the subject's linear or angular velocity or acceleration.

Upon determining that the subject is in an unacceptable state, the processor module 24 determines how the subject should move in order to be in an acceptable state. For example, an acceptable state may be one in which the subject stands within a pre-determined angular threshold from vertical. In such a case, the processor module 24 may determine that the subject is leaning too far to the left, and that the subject should lean more to the right. When the processor module 24 determines that the subject should move in a particular manner, it sends a signal to an actuator 26, which is connected to a stimulator 28. The actuator 26 activates the stimulator 28 to provide the subject with a stimulus indicating the manner in which he should change his orientation in order to achieve an acceptable state. The stimulator 28 may be mounted on any combination of the sensory substitute devices $20_1, 20_2, \ldots, 20_n$, or it may be a separate unit.

The stimulator 28 may provide electrical, tactile, auditory, or visual stimulation. Electrical stimulation may be provided, for example, by stimulating the subject with a low-ampere electrical current. Tactile stimulation may be provided, for example, by the use of vibrating elements positioned in an array about the subject's torso. Audio stimulation may be provided, for example, by providing an audio message to the subject via headphones worn by the subject. Visual stimulation may be provided, for example, through a display incorporated in a pair of eyeglasses worn by the subject.

Figure 2B:
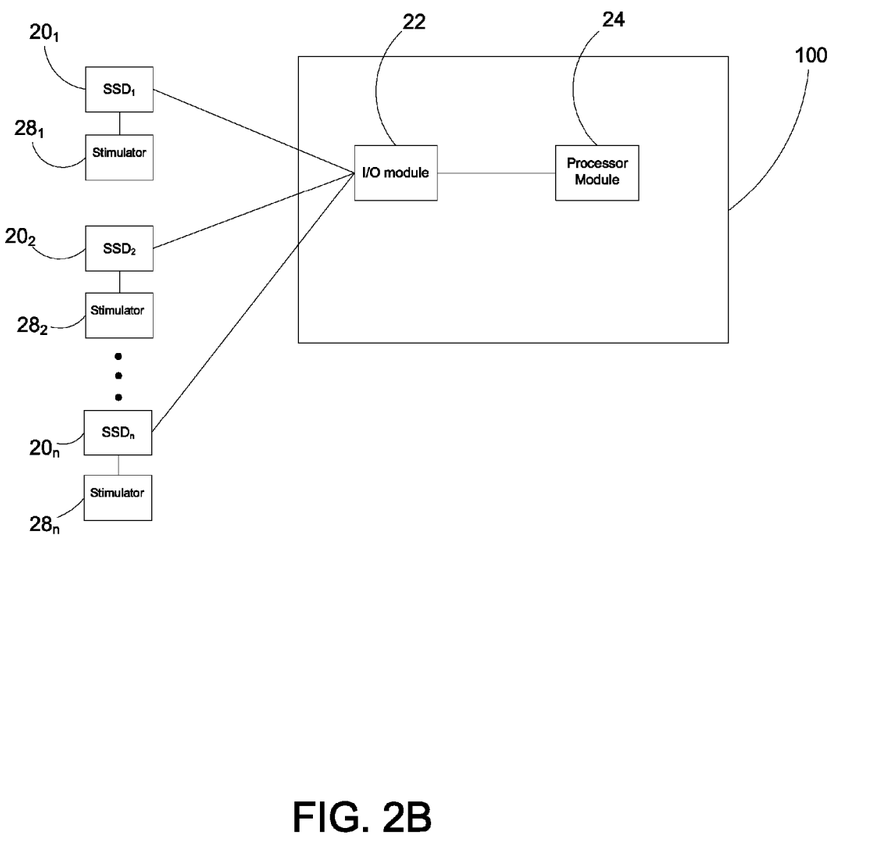

In another implementation, shown in FIG. 2B, the integration system 100 includes an input/output module 22, and a processing module 24. Sensory substitution devices $20_1$, $20_2$, ..., $20_n$ are connected to the integration system 100 through the input/output module 22. Some or all of the sensory substitution devices $20_1$, $20_2$, ..., $20_n$ are connected to one or more stimulators $28_1$, $28_2$, ..., $28_n$. In this implementation, the integration system 100 need not contain an actuator 26. Instead, each sensory substitution device $20_1$, $20_2$, ..., $20_n$ drives its own stimulator.

Figure 2C:
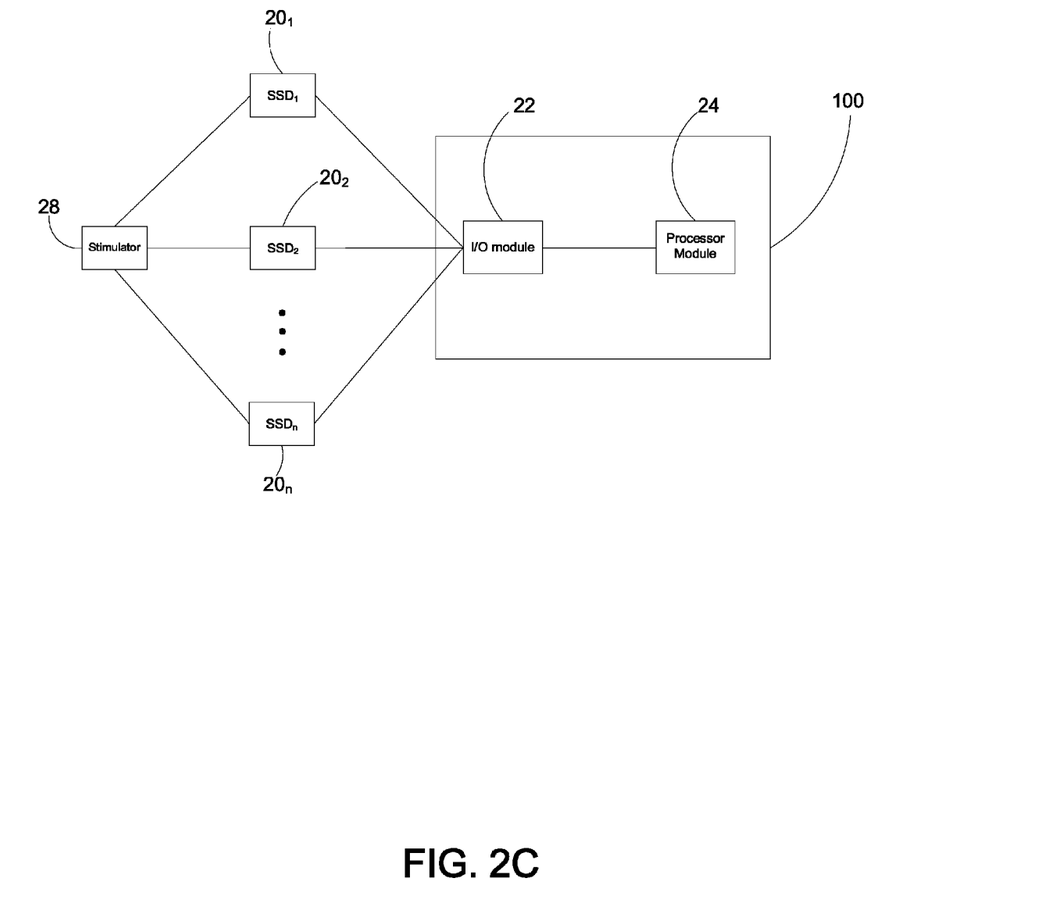

In another implementation, shown in FIG. 2C, the integration system 100 includes an input/output module 22, and a processing module 24. Sensory substitution devices $20_1$, $20_2$, ..., $20_n$ are connected to the integration system 100 through the input/output module 22. Some or all of the sensory substitution devices $20_1$, $20_2$, ..., $20_n$ are connected to a single stimulator 28.

In any of the above implementations, any or all of the integration system 100, the sensory substitution devices $20_1$, $20_2$, ..., $20_n$, or the stimulator 28 can include a battery for providing power to the respective units, and a wireless transmitter/receiver to communicate with other units.

Based on the inputs of the sensory substitution devices $20_1$, $20_2$, ..., $20_n$, the processor module 24 determines a "context" in which the subject finds himself. A context is a pre-defined set of one or more states. Typically, a context corresponds to a common activity. For example, in one context, the subject is in a state in which: (1) his torso is within a pre-determined angular threshold from vertical; and (2) there is less than a pre-determined threshold of pressure on his feet. This context corresponds to "sitting." Other exemplary contexts include "rising," in which a previously sitting subject puts pressure on his feet and inclines his torso at a relatively great angle from vertical; "walking" in which the subject's weight is distributed along his feet in a pre-defined pattern, e.g., beginning with heel strike and ending with toe pressure, alternating from foot to foot; "walking up stairs," in which the subject's weight alternates from the front portion of one foot to the front portion of another foot; "carrying a load," in which pressure in excess of the subject's weight is detected on the subject's feet for a pre-determined amount of time; "slipping," in which all pressure is abruptly taken off one foot, accompanied by a rapid change of angular orientation. Other contexts may be determined with the sock/vest combination, and still other contexts may be determined with input from sensory substitution devices instead of, or in addition to, a sock or a vest.

Words used to describe contexts (e.g. "sitting," "walking," etc.) are labels of convenience, and do not imply any description of the subject beyond the defining characteristics of the context. For example, the integration system 100 may determine the context of the subject to be "walking," when in fact the subject is running. In general, a subject's context need not only be determined by the subject's state at a particular time, but may also be based on the subject's previous states or contexts. For example, the "rising from a chair" context results only after the subject has been in the "sitting in a chair" context.

As explained more fully below, knowledge of the subject's context allows the integration system 100 to effectively present stimulus to the subject, to dynamically update a definition of an acceptable state, and to efficiently manage its resources and the resources of the sensory substitution devices $20_1$, ..., $20_n$.

Effective Presentation of Stimulus

One way in which stimulus is more effectively presented is by weighting the inputs from the sensory substitution devices $20_1$, $20_2$, ..., $20_n$ in terms of importance, and integrating them into a feedback signal optimized for the wearer's specific context.

For example, while walking, vestibular sensory information is important when the subject's heel is striking the ground. Thus, in an exemplary embodiment in which a vest and a sock are used as sensory substitution devices, when the integration system 100 determines the subject's context to be "walking," it presents motion cues on the basis of when the subject's heel strikes the ground, as detected by the sock.

In another example, when the subject is rising from a chair, his natural mechanics suggests that his torso should be inclined at a relatively large angle just as he begins to lift himself with his feet. The transition from sitting to standing vertically typically takes approximately 1 second, but generally varies from subject to subject. Thus, in an exemplary embodiment using the vest and the sock, the subject would not be prompted to align himself with the vertical until a pre-determined amount of force has been applied to his feet, or a pre-determined amount of time sufficient for the subject to align himself has passed.

In another example, the subject may be particularly adept at moving through a certain area, for example, the subject's home or place of employment. Thus, stimulus may be safely turned off when the subject is in this area. In such cases, the integration system 100 determines whether the subject is in this area using the positioning transmitter or receiver. For example, the area may be defined by boundaries specified in GPS coordinates, or the area may be defined as a pre-defined distance from a positioning beacon.

In another example, the subject may only need stimulation when he is engaged in potentially disorienting activities. Such activities include piloting an aircraft or moving underwater. In this example, the integration system 100 only stimulates the subject if, for example, an altimeter determines the subject's altitude to be greater than (for piloting an aircraft) or less than (for moving underwater) a pre-determined threshold.

In another example, a subject may have difficulty in maintaining an acceptable state when outdoors. In such cases, the integration system 100 can use a photocell or a thermometer to help determine that the subject is outdoors. For example, a measured ambient temperature may be compared to a known outdoor ambient temperature, or the light incident on the subject may be compared to typical levels of outdoor sunshine.

Dynamically Updating Acceptable States

In the absence of an integration system 100, sensory substitution devices will drive the subject towards a pre-defined acceptable state or orientation, such as an upright orientation, without regard to the subject's activity or context. Integrating various sensory substitution devices, as described herein, allows dynamically updating the definition of an acceptable state or orientation on the basis of the subject's probable activity, as determined by the subject's context.

For example, there are a number of contexts in which an acceptable orientation is not aligned with vertical. When walking, for example, the human body's natural mechanics are such that one's torso is optimally pitched slightly forward. The pitch angle increases as the person's speed increases. Similarly, the mechanics of the human body make a forward pitch desirable when going up stairs. Also, when standing on a slope, it is desirable to pitch slightly forward when facing uphill and slightly backward when facing downhill.

Thus, in an exemplary embodiment, when the integration system 100 determines the subject's context to be "walking," the subject is encouraged to maintain a forward pitch by an angle based on his speed, as measured by the interval between pressure changes detected by the sock. Additionally the integration system 100 can determine, from pressure signatures provided by the sock, that the subject is going up stairs, or that the subject is standing on a slope.

In another example, integrating the sensory substitution data can be advantageous when the subject is carrying a load. Generally, it is desirable that a subject stand with his center of mass over his base of support. When not carrying a load, this is essentially equivalent to the subject standing aligned with the vertical. However, when the subject is carrying a load, it is desirable for the center of mass of the subject-plus-load combination to be over his base of support. When the load is carried off-center in a particular direction (e.g., over the subject's left shoulder on the subject's back), the subject is encouraged to lean in an antipodal direction (e.g., forward and to the right).

In an exemplary embodiment in which the sensory substitution devices include a vest and a sock, the sock detects the weight of the load and, based on the change in pressure signature from the nominal case, can determine generally where the load is being carried. On the basis of this determination, the integration system 100 drives the subject to attain an orientation that deviates from the vertical to extent needed to compensate for the weight of the load.

In another example, integrating sensory substitution data can be advantageous in wet or rainy conditions, where the likelihood of slipping may be greater. If in dry conditions, a subject is stimulated to maintain an orientation within a predetermined threshold of vertical, then in rainy conditions the subject is stimulated to maintain an orientation within a smaller threshold of vertical. In some circumstances, stimulating the subject to remain more upright may cause the subject to tread with greater care, and therefore be less likely to slip.

Thus, in an exemplary embodiment in which a sensory substitution device includes a moisture sensor, the integration system 100 causes the subject to be stimulated to maintain an orientation within a threshold of vertical, where the threshold is a nonincreasing function of the moisture in the subject's environment.

One way a sensory substitution device can be configured is as a control system. Generally, a control system monitors and adjusts the properties of another system, e.g the subject, and causes those, or other, properties to move towards desired or acceptable values. The ensemble of desired or acceptable values is referred to as a "set-point." Although the term "point" is used, there may be a range of such values. The subject is referred to as the controlled system. For the purposes of the sensory substitution device, the subject is characterized by the physical characteristics detected by the sensory substitution device; i.e. the subject's state.

One tool for understanding the operation of a control system is that of a "state space" of the subject. The state space is the collection of all possible states the subject can be in. The full state space of the subject is often multi-dimensional. However, the phrase "state space" will also be used to refer to two- or three-dimensional slices of the full state space that are under consideration.

Figure 3:
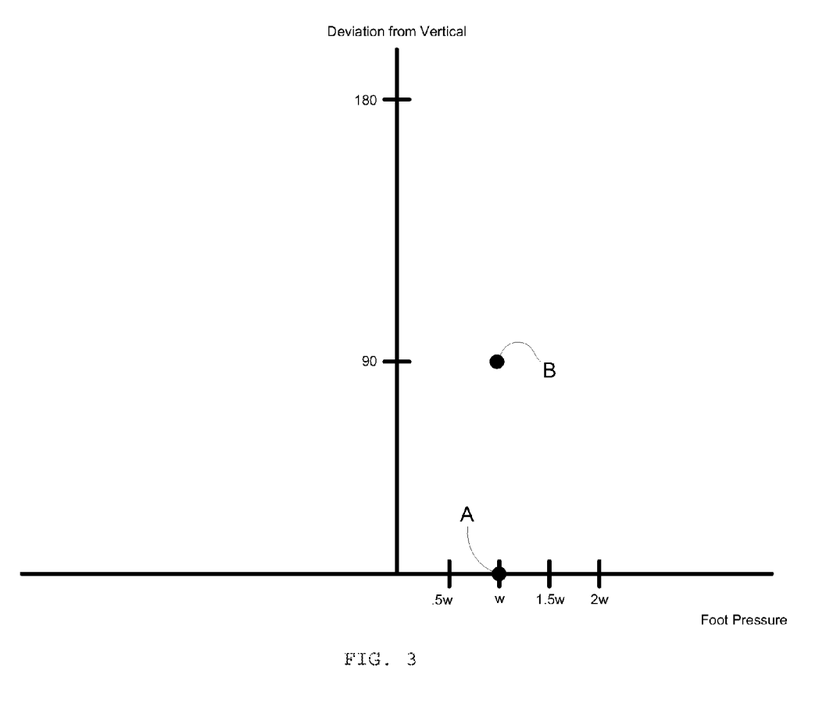
FIG. 3 is exemplary depiction of a subject's state space.

For example, FIG. 3 shows a two-dimensional slice of state space. The horizontal axis represents the total pressure on the subject's feet measured in multiples of the subject's weight w, and the vertical axis represents the angle at which the subject's torso is inclined with respect to vertical, measured in degrees. Thus, the point A represents the a state in which the subject stands vertically. The point B represents a state in which the subject is bent over with his torso is 90 degrees off vertical.

In the absence of an integration system 100, a control system that relies on an individual sensory substitution device 20 will recognize a set-point and drive the subject's state towards the set-point. When different sensory substitution devices $20_1, 20_2, \ldots, 20_n$ are integrated using the integration system 100, the set-point of one sensory substitution device $20_1$ can be changed by the integration system 100 in light of data obtained from other sensory substitution devices $20_2, \ldots, 20_n$.

Figure 4:
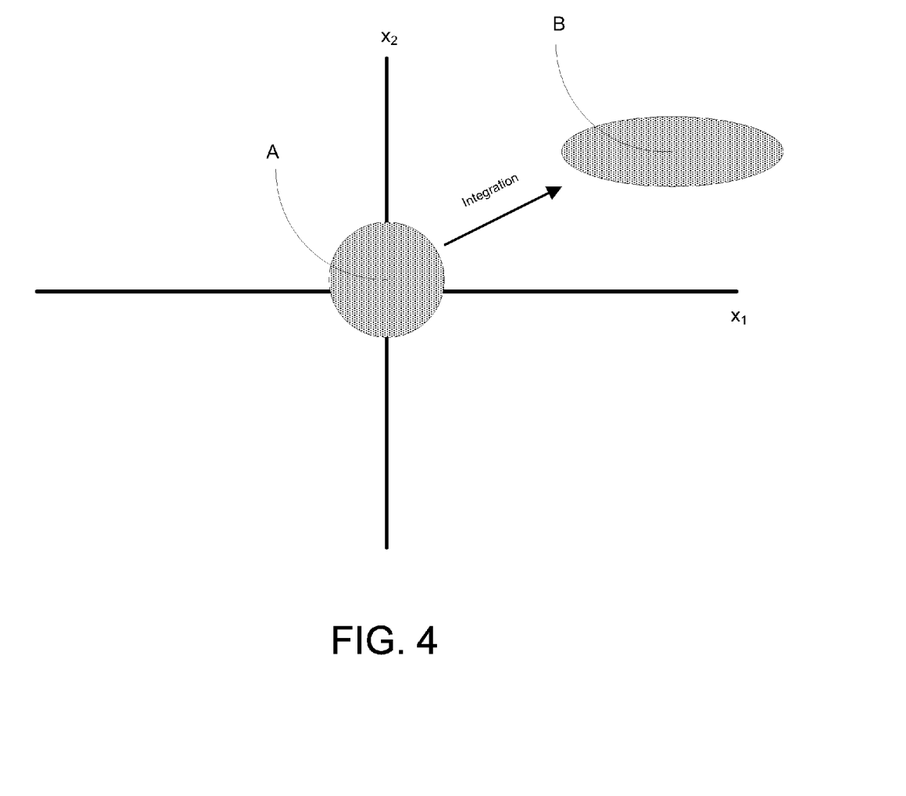
FIG. 4 shows exemplary set-points based on integrated and non-integrated sensory substitution devices.

FIG. 4 shows a general two dimensional slice of phase space with $x_1$ and $x_2$ axes provided. The variables $x_1$ and $x_2$ can be any physical characteristics of the subject. Region A is an exemplary set-point associated with the sensory substitution device $20_1$ in the absence of an integration system 100. Region B is an exemplary set-point for the same device $20_1$ as determined by the integration system 100 in communication with one or more additional sensory substitution devices $20_2, \ldots, 20_n$. In this example, the integration system 100 has transformed the set-point of the sensory substitution device $20_1$ in light of data obtained by other sensory substitution devices $20_2, \ldots, 20_n$.

Figure 5:
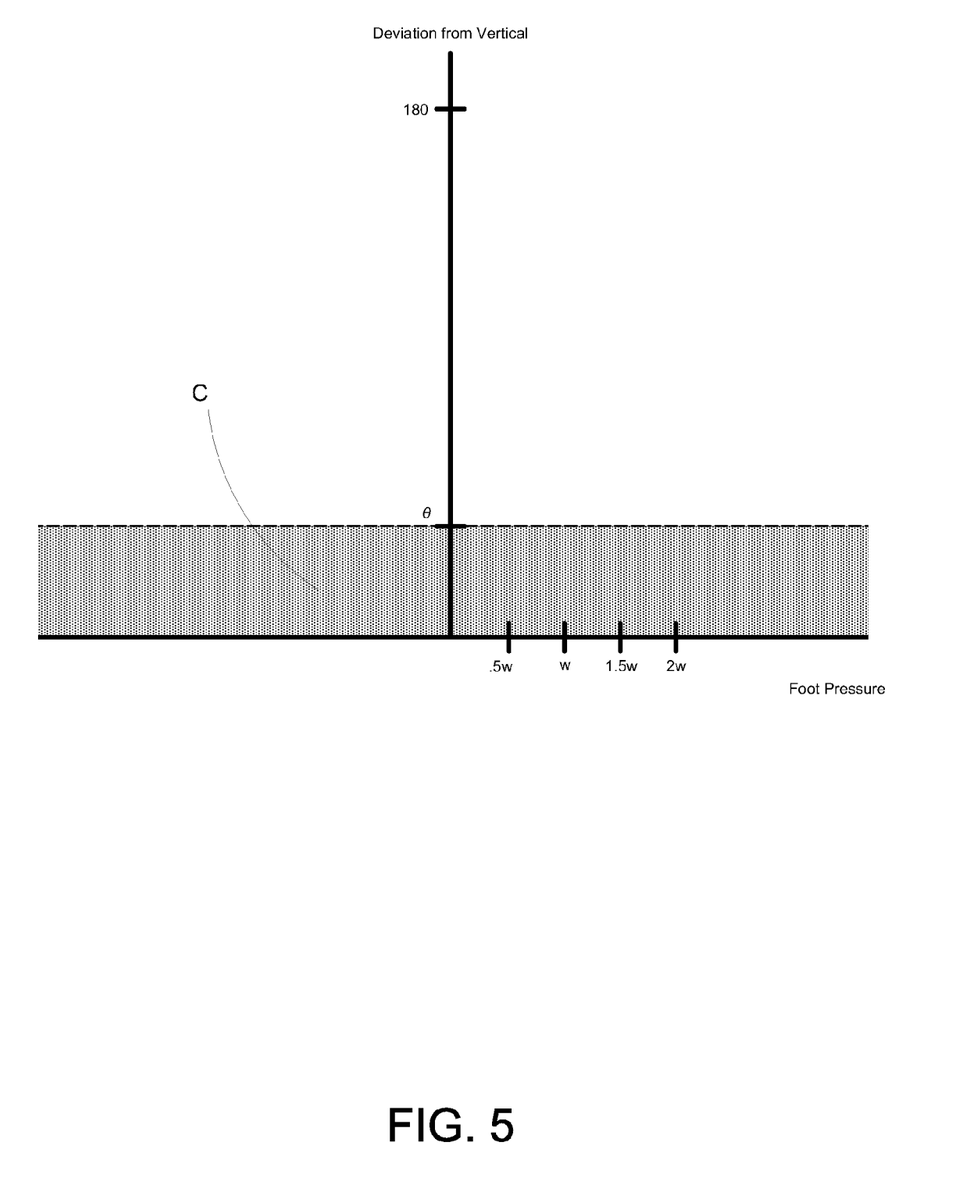
FIG. 5 shows a set-point based on non-integrated sensory substitution devices.

For example, consider a subject outfitted with sensory substitution devices $20_1, \ldots, 20_n$ including vest and sock, in the absence of an integration system 100. FIG. 5 shows a state space of a subject, with axes as in FIG. 3. Region C is the set-point associated with the vest. It corresponds to the portion of state space in which the subject's deviation from vertical is within θ degrees, regardless of the pressure on the subject's feet. Thus, when the vest detects that the subject's deviation from vertical is less than θ, orientation cues are not provided to the subject. When the vest detects the subject's deviation from vertical is more than θ, orientation cues are provided to let the subject know how he should move in order to decrease his deviation from vertical.

For sensory substitution devices $20_1, \ldots, 20_n$ in the absence of an integration system 100, the set-point for a particular device is independent of measurements made by other devices. For example, Region C is the set-point for the vest, regardless of whether the sock shows increased pressure, indicating the subject is carrying a load. Thus, when the subject is carrying a load, the subject will be encouraged to remain within θ degrees of vertical, even if such an orientation results in the center of mass of the subject-plus-load combination not being over the subject's base of support.

Figure 6:
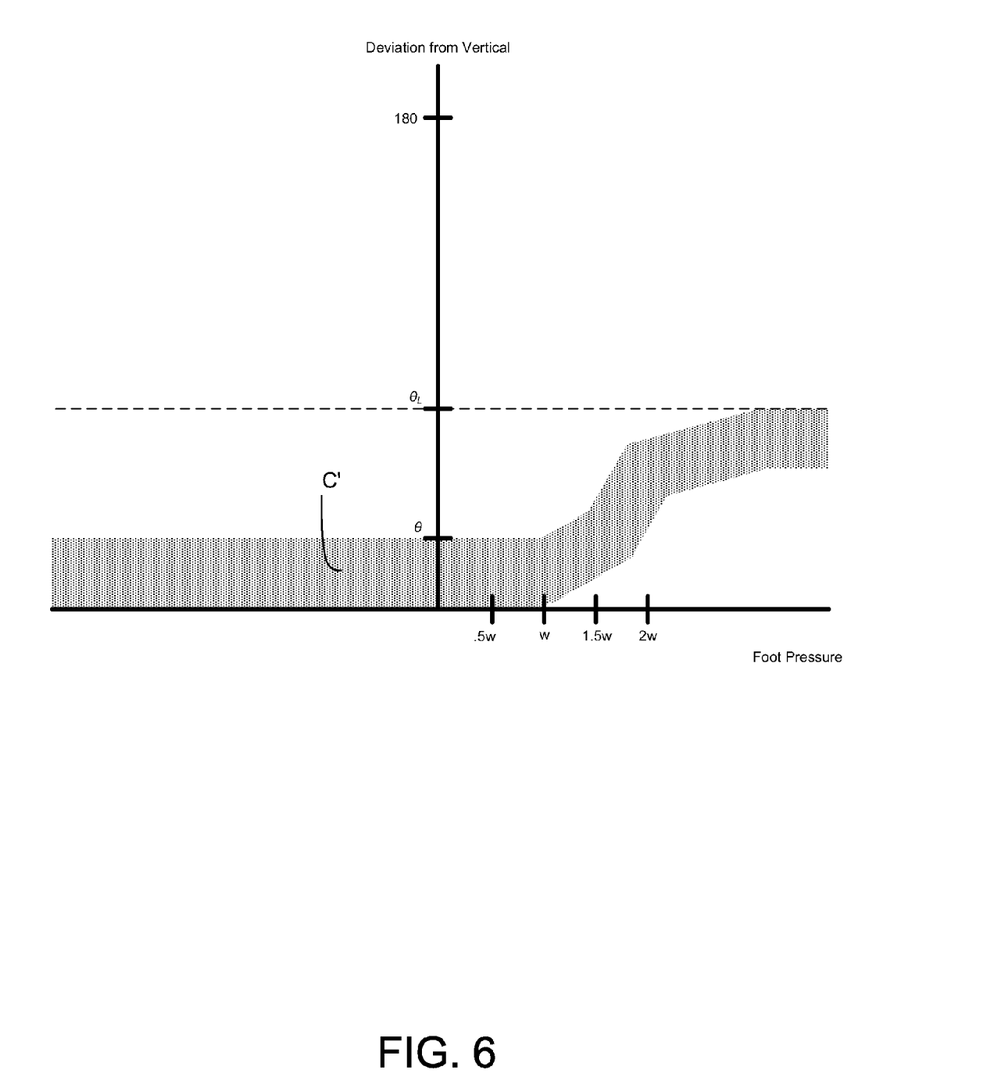
FIG. 6 shows a dynamically updated set-point based on integrated sensory substitution devices.

FIG. 6 depicts the same state space, but with a set-point in which acceptable values for one sensory substitution device output depend on values for another sensory substitution device output. In this example, Region C' is the set-point associated with the context of carrying a load. When the sock detects pressure equal to or less than w, the subject is provided cues so as to remain within an angle θ of vertical, as in the non-integrated case. However, as the pressure detected by the sock increases, the subject may be encouraged to lean in a direction antipodal to the location of the load. (The direction of the lean is not illustrated here for simplicity, but may be accounted for by adding another dimension to this state space depiction.) A set-point according to Region C' will only encourage the subject to maintain a maximum lean of $θ_L$. The value $θ_L$ is determined from the particular physical attributes and medical needs of the subject.

The set-point C' is only valid when the integration system 100 determines the subject's context to be "carrying a load."

If the integration system 100 determines that the context is, for example, "sitting," the set-point will occupy a different portion of state space.

Figure 7:
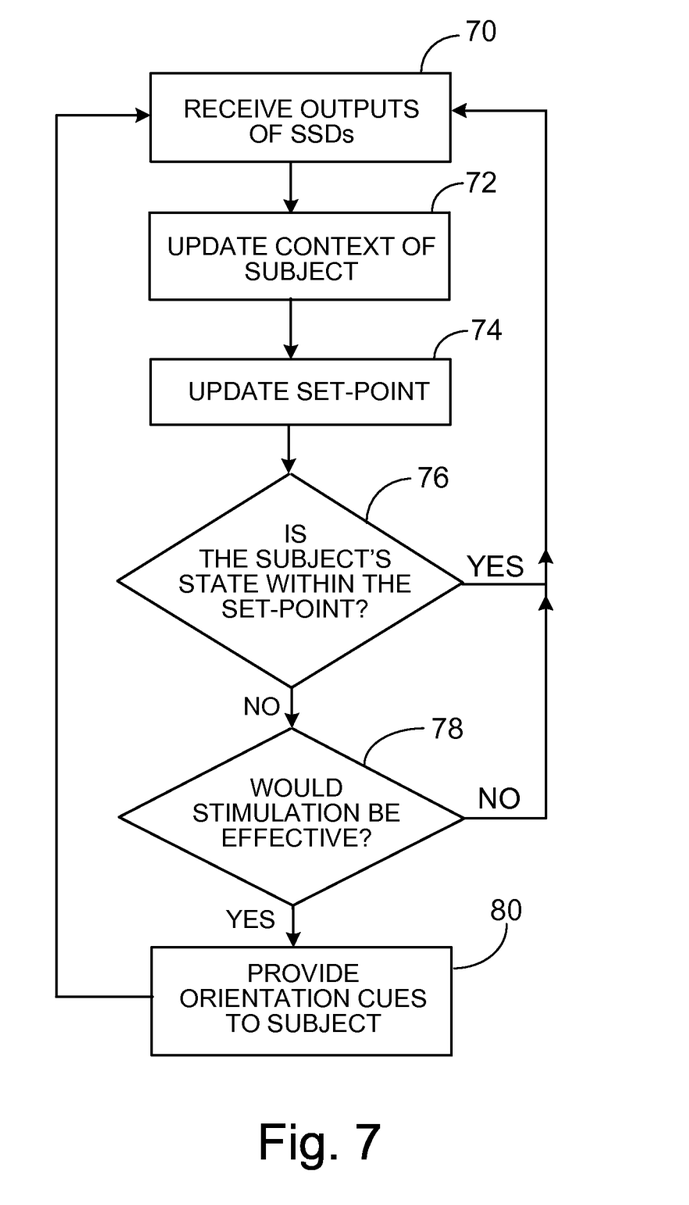
FIG. 7 shows a flowchart illustrating a use of the sensory data integration system.

FIG. 7 is a flow chart describing one possible use of a sensory integration system 100. The integration system 100 receives the outputs of the sensory substitution devices $20_1$, $20_2$, ..., $20_n$ (step 70). Based on the outputs, the integration system 100 updates the subject's context (step 72), and the subject's set-point (step 74). As used here, "updating" the context or set-point includes maintaining the context's or set-point's previous values or definitions, as well as changing the context or set-point.

The set-point may be changed if the subject's context changes. For example, if the integration system 100 determines that subject is carrying a load (and was not previously carrying the load), the integration system 100 changes the set-point so as to encourage the subject to compensate for the load by leaning in a particular direction.

The set-point may be changed even though the subject's context does not change. For example, if the subject's context is "walking," then the subject is encouraged to pitch forward with an angle proportional to the subject's speed. If the subject increases his speed (but remains in the "walking" context), then the set-point will be changed to encourage the subject to maintain a greater forward pitch.

The subject's state is tested against set-point (step 76). If the subject's state is within the set-point, then no orientation cues are provided. Otherwise, based on the subject's context and state, the integration system 100 determines 78 whether stimulation would be effective if presented to the subject. For example, if the subject's context is "walking," then the integration system 100 determines if the subject's state is sufficiently close to heel-strike. If stimulation would be effectively presented, then orientation cues are provided 80 to the subject.

Efficient Management of Resources

Resources such as battery life can be managed by powering down certain sensory substitution devices $20_1$, $20_2$, ..., $20_n$ when, based on the subject's context, they are not likely to provide helpful orientation cues. For example, if the subject's context is sitting or lying down, it is less likely that the subject will need cues to remain vertical. Thus, the integration system 100 powers down those sensory substitution devices $20_1$, $20_2$, ..., $20_n$ that provide such cues. In an exemplary embodiment, all the sensory substitution devices $20_1$, $20_2$, ... $20_n$ will be powered down except those necessary to detect a change in the subject's context. In the exemplary embodiment in which the sensory substitution devices $20_1$, $20_2$, ..., $20_n$ include a vest and sock, the vest will be powered down after the subject has been sitting or lying down for a pre-determined amount of time.

What is claimed is:

1. A system for determining and providing orientation cues to a subject, the system comprising:
   (a) a first sensory substitution device configured to obtain first data related to a first state of the subject, wherein the first sensory substitution device is selected from a group consisting of a vibratometer configured to detect a vibration in the subject, a magnetometer configured to measure an ambient magnetic field, an altimeter, and an electromyography device configured to detect activity in a muscle of the subject;
   (b) a second sensory substitution device configured to obtain second data related to a second state of the subject, the second state including a motion and an orientation of the subject;
   (c) a processor configured to:
      determine at least in part on the basis of a combination of the first data and the second data, an updated context of the subject,
      dynamically update a definition of an acceptable region within a state space defined by at least the first and second states, based on the updated context of the subject,
      determine a deviation of a position of the subject from the updated acceptable region within the state space, and
      determine an orientation cue for the subject wherein the cue indicates in which particular manner and direction the subject should change the subject's orientation to reduce the deviation; and
   (d) a stimulator for providing the orientation cue to the subject, wherein the orientation cue is selected from a group consisting of a tactile cue, an audio cue, a visual cue, and an electrical cue.

2. The system of claim 1, wherein the first sensory substitution device is configured to be deactivated based on the context.

3. The system of claim 1, wherein the second data is indicative of a pressure on the subject's foot.

4. The system of claim 1, wherein the first sensory substitution device is configured to obtain data indicative of when a subject's heel strikes the ground.

5. The system of claim 1, wherein determining the updated context comprises determining that the subject is rising from a chair, and wherein the stimulator is configured to provide the orientation cue following a time sufficient to allow the subject to transition from a sitting position to a standing position.

6. The system of claim 1, wherein the processor is configured to determine the updated context by determining that the subject is standing on a slope.

7. The system of claim 1, wherein the processor is configured to determine the updated context by determining that the subject is walking up stairs.

8. The system of claim 1, wherein the processor is configured to determine the updated context by determining that the subject is walking, and wherein the stimulator is configured to provide a cue selected to encourage the subject to maintain a forward pitch.

9. The system of claim 1, wherein the processor is configured to determine the updated context by determining that the subject is carrying a load, and wherein the stimulator is configured to provide a cue selected to encourage the subject to lean in an antipodal direction.

10. The system of claim 1, wherein the processor is configured to determine the updated context by determining that wet conditions prevail, and wherein the stimulator is configured to provide an orientation cue selected to encourage the subject to maintain a pitch angle within a selected threshold of vertical, the selected threshold being dependent on whether wet or dry conditions prevail.

11. The system of claim 1, wherein the processor is configured to determine the updated acceptable region within the state space based on the subject's probable activity.

12. The system of claim 11, wherein the processor is further configured to determine the subject's probable activity based on the updated context.

13. The system of claim 1, wherein the processor is further configured to determine the position of the subject within the state space based on the first data and the second data.

14. The system of claim 1, wherein the processor causes the stimulator to provide the orientation cue upon determining that the deviation of the position of the subject from the updated acceptable region is sufficiently high.

15. The system of claim 14, wherein the updated acceptable region within the state space is determined based on the subject's probable activity.

* * * * *